United States Patent [19]

Maulding

[11] Patent Number: 5,001,254

[45] Date of Patent: Mar. 19, 1991

[54] METHOD FOR THE PREPARATION OF QUINOLINE-2,3-DICARBOXYLIC

[76] Inventor: Donald R. Maulding, 57 Katydid Dr., Somerville, N.J. 08876

[21] Appl. No.: 196,165

[22] Filed: May 19, 1988

Related U.S. Application Data

[62] Division of Ser. No. 902,275, Aug. 29, 1986, Pat. No. 4,766,218.

[51] Int. Cl.$^5$ .................................. C07C 101/453
[52] U.S. Cl. ................................. 560/44; 546/170; 560/171
[58] Field of Search .............. 560/44, 171; 546/170

[56] References Cited

U.S. PATENT DOCUMENTS 4,675,432  6/1987  Maulding .............................. 560/44
4,814,486  3/1989  Maulding .............................. 560/44

Primary Examiner—Paul J. Killos
Attorney, Agent, or Firm—E. J. Tsevdos

[57] ABSTRACT

The present invention relates to novel methods for the preparation of quinoline-2,3-dicarboxylic acid, useful for the preparation of the highly effective 2-(2-imidazolin-2-yl)quinoline-3-carboxylic acid herbicidal agents.

7 Claims, No Drawings

METHOD FOR THE PREPARATION OF QUINOLINE-2,3-DICARBOXYLIC

This is a division of application Ser. No. 902,275 filed Aug. 29, 1986, now U.S. Pat. No. 4,766,218, issued Aug. 23, 1988.

BACKGROUND OF THE INVENTION

The present invention relates to novel methods for preparing quinoline-2,3-dicarboxylic acids. These acids are useful intermediates in the preparation of herbicidal pyridine and quinoline imidazolinone herbicidal compounds.

The herbicidal pyridine and quinoline imidazolinone compounds prepared from the present compounds include 2-(4-isopropyl-4-methyl-5-oxo-2-imidazolin-2-yl)quinoline-3-carboxylic acid, esters and salts thereof and are disclosed in European Patent Application No. 0 041 623, (incorporated herein by reference). These herbicidal imidazolinyl quinolinecarboxylic acids may be prepared by the procedure described in U.S. Pat. No. 4,518,780 (incorporated herein by reference) by cyclization, under basic conditions, an appropriately substituted 2-carbamoyl quinoline-3-carboxylic acid that, in turn, is prepared by the reaction of a substituted quinoline-2,3-dicarboxylic acid anhydride and appropriately substituted aminocarboxamide or aminothiocarboxamide. Quinoline-2,3-dicarboxylic acid anhydrides are prepared from the diacids by procedures well known in the art. However, the diacids themselves are not readily available.

Pending application for U.S. patent of Robert Doehner, Ser. No. 698,192 filed Feb. 4, 1985 (incorporated by reference) describes a method useful for the preparation of quinoline-2,3-dicarboxylic acid and esters thereof by reacting a beta-anilino-alpha,beta-unsaturated ester with an immonium salt (commonly called a Vilsmeier reagent). The beta-anilino-alpha,beta-unsaturated esters are obtained by the reaction of appropriately substituted anilines with keto-esters or dialkyl acetylene dicarboxylates. This overall reaction for the preparation of quinoline-2,3-dicarboxylates is illustrated in Flow Diagram I.

FLOW DIAGRAM I

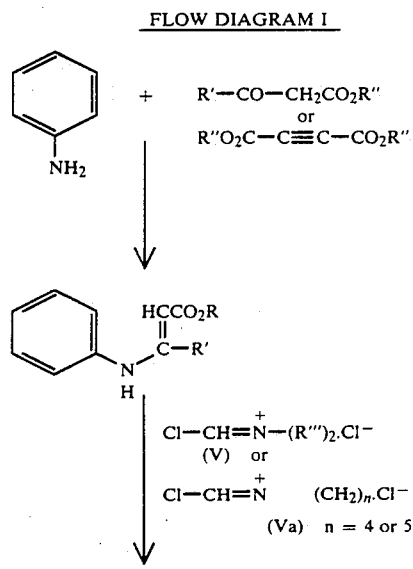

-continued
FLOW DIAGRAM I

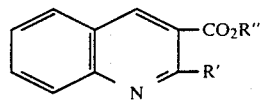

wherein R' is $CH_3$ or $CO_2R''$ and R'' is $C_1-C_4$ alkyl and R''' is $CH_3$ (or $C_1-C_4$ alkyl).

When R' is $CH_3$, the diacid is obtained by concurrent oxidation and hydrolysis of the product under aqueous basic conditions in the presence of nickel peroxide as described in U.S. Pat. No. 4,459,409 (incorporated herein by reference).

Unfortunately, the availability of ketoesters and dialkyl acetylene dicarboxylates, such as diethyloxalacetate and diethyl acetylenedicarboxylate, is limited, thus restricting the quantities of anilino-fumarate and quinoline-2,3-dicarboxylic acid, the intermediate required for preparing herbicidal 2-(4-isopropyl-4 -methyl-5-oxo-2-imidazolin-2-yl)quinoline-3-carboxylic acid, esters and salts thereof.

SUMMARY OF THE INVENTION

The present invention overcomes this limitation in providing a source of the quinoline-2,3-dicarboxylic acid, esters and salts thereof through the reaction of a dichlorosuccinate and amine to form anilinofumarate. With a ready source of anilinofumarate, an efficient and novel method for a ready source of quinoline-2,3-dicarboxylic acid is available for production of the herbicides, 2-(4-isopropyl-4-methyl-5-oxo-2-imidazolin-2-yl)quinoline-3-carboxylic acid, esters and salts thereof.

It is an object of the present invention, therefore, to provide a novel method for the preparation of anilinofumarate utilizing dichlorosuccinates, obtainable from dialkyl maleates. These are readily available in large quantities and hence provide a method for the manufacture of large quantities of quinoline-2,3-dicarboxylic acid and esters thereof for the subsequent production of herbicidal 2-(4-isopropyl-4-methyl-5-oxo-2-imidazolin-2-yl)quinoline-3-carboxylic acid, esters and salts.

It is another object of the present invention to provide a novel method to prepare dialkyl oxalacetates as precursors for anilinofumarates.

These and further objects will become more apparent by the detailed description of the invention provided hereinbelow.

DETAILED DESCRIPTION OF THE INVENTION

The present invention relates to novel methods for the preparation of anilinofumarate and quinoline-2,3-dicarboxylic acid and esters thereof, said method comprises reacting a dichlorosuccinate (formula I)

wherein R is $C_1-C_4$ alkyl with a minimum of 3 molar equivalents (3 molars or greater) of an amine having the formula II

wherein $R_1$ and $R_2$ are each H or $C_1$-$C_6$ alkyl, with the proviso that only one of $R_1$ or $R_2$ is H; or when taken together $R_1$ and $R_2$ with the nitrogen atom to which they are attached may form a 5 or 6 membered ring containing at most 2 heteroatoms; in an inert solvent, at a temperature of about 25° C. to reflux for about 1 to 24 hours to form the resulting mixture of alkylaminomaleate or alkylaminofumarate (IIIa),

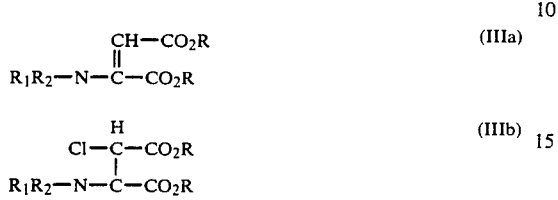

wherein R, $R_1$ and $R_2$ are as defined above; and further reacting the resulting mixture of alkylaminomaleate or alkylaminofumarate and chloroaminosuccinate of formula IIIa and IIIb with a molar equivalent of aniline in an organic solvent, optionally containing an organic acid, such as acetic acid, at a temperature of about 25° C. to 90° C. for about 1 to 24 hours, and isolating the thus-formed anilinofumarate.

Alternatively, the formula (IIIa) alkylaminomaleates or alkylaminofumatates and chloroamino succinates (IIIb) may be hydrolyzed with aqueous acid to yield dialkyl oxalacetates which may then be reacted with aniline, as described in co-pending application for U.S. patent of R. Doehner Ser. No. 698,192, filed Feb. 4, 1985, incorporated herein by reference.

Quinoline-2,3-dicarboxylate acid then is prepared from the thus-formed anilinofumarate by reaction with an approximately equimolar amount of a Vilsmeier reagent in the presence of a hydrocarbon solvent, such as toluene or a chlorinated hydrocarbon solvent such as methylene chloride, dichloroethane, orthodichlorobenzene, chlorobenzene, or mixtures thereof, at a temperature of about 40° C. to 110° C., for a period of time sufficient to essentially complete the reaction and yield a dialkyl quinoline-2,3-dicarboxylate. That is then hydrolyzed under either acid or basic conditions, to yield quinoline-2,3-dicarboxylic acid. This procedure also is described in pending U.S. patent application No. 698,192, incorporated herein by reference.

The described reactions are illustrated by Flow Diagrams IIa-c hereinbelow.

FLOW DIAGRAM IIA

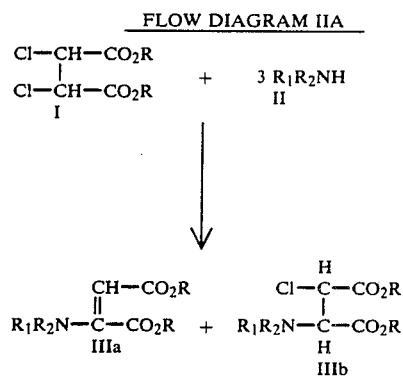

FLOW DIAGRAM IIb

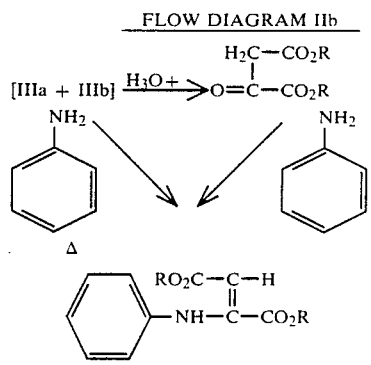

FLOW DIAGRAM IIc

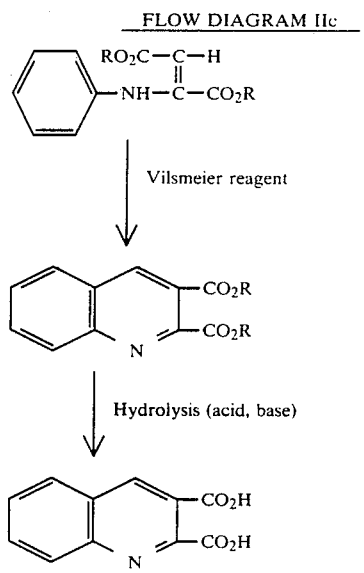

wherein R, $R_1$ and $R_2$ are as described above.

Surprisingly, it has been found that diethyl anilinofumarate or diethyl oxalacetate, and hence quinoline-2,3-dicarboxylic are prepared, in high yields, by the method of the present invention. In accordance with the method of this invention, diethyl dichlorosuccinate, which may be prepared by the method described in Japanese Patent No. 71 21,564 incorporated herein by reference, is reacted with 3 molar equivalents of diethylamine in toluene at 80° C. to 85° C. for 7 hours and then at reflux for 3 hours. The reaction mixture is cooled to room temperature, washed with water and the solvent evaporated off to give the formula IIIa and IIIb products (in a ratio of IIIa/IIIb of 7.5/1) wherein $R_1$ and $R_2$ are each ethyl. Solvents suitable for the reaction of dichlorosuccinates with formula II amines include hydrocarbons, aromatic hydrocarbons, halogenated hydrocarbons and aromatic hydrocarbons.

Diethyl anilinofumarate is prepared by adding a molar equivalent of aniline to a toluene solution (20 mL) of the mixture of formula IIIa and IIIb compounds prepared above, containing 5 molar equivalents of acetic acid. The reaction mixture is then stirred at 80° C. to 85° C. for 4 hours. The product is isolated in 85% to 90% yields after cooling the mixture to room temperature and washing the organic solution with water and then dilute hydrochloric acid and evaporating off the solvent.

Solvents suitable for the reaction of aniline with formula IIIa and IIIb compounds include hydrocarbons, aromatic hydrocarbons and halogenated hydrocarbons and aromatic hydrocarbons. Further, it has been found that while the above reaction proceeds in the absence of an organic acid, that significantly higher yields of anilinofumarate are obtained in shorter reaction times in the presence of organic acids such as acetic, propionic and the like. Thus, while the above reaction yields 80% to 90% of the desired product after 4 hours at 80° C. to 85° C. in the presence of acetic acid, refluxing the reactants in the absence of an organic acid for 10 hours yields only 40% anilinofumarate.

The method of the present invention is further exemplified by the following examples which are illustrative and not limitative thereof.

EXAMPLE 1

Preparation of dichlorosuccinate $$\begin{array}{c} HC-CO_2C_2H_5 \\ \parallel \\ HC-CO_2C_2H_5 \end{array} + Cl_2 \xrightarrow[\text{(cat)}]{\text{EtOH}} \begin{array}{c} Cl-CH-CO_2C_2H_5 \\ | \\ Cl-CH-CO_2C_2H_5 \end{array}$$

Chlorine gas is bubbled into an ethylene dichloride solution of diethyl maleate containing ethanol, (0.1 molar equivalents). After stirring the mixture at room temperature for 8 hours, it is flushed with nitrogen gas for 5 minutes and the solvent removed under reduced pressure to yield the dichlorosuccinate in 94% yield.

EXAMPLE 2-5

Preparation of diethyl diethylaminomaleate and diethyl 2-chloro-3-diethylaminosuccinate

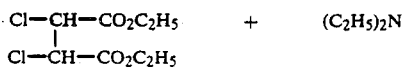

Diethylamine (2.41 g, 0.033 mol) is added dropwise to stirred solution of diethyl dichlorosuccinate (2.59 g, 0.01 mol) in toluene (15 mL). The resulting mixture is heated at 80° C. to 85° C. for 8 hours and then at reflux for 3 hours. After cooling the reaction mixture to room temperature, it is washed with water (15 mL) and the toluene layer is separated off and evaporated under reduced pressure to yield 2.07 g (85%) of the mixture of diethyl diethylaminomaleate and the title chloro-amino succinate in a maleate to succinate ratio of 7.5/1.

Utilizing the above procedure and substituting the appropriate amine for diethylamine yields the products listed in Table I.

TABLE I

| Example | Amine | % Yield (maleate & succinate) | Maleate to succinate Ratio |
|---|---|---|---|
| 3 | 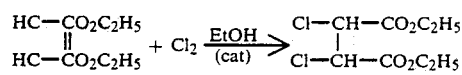 | 86 | 4:1 |
| 4 | HNC₄H₉n | 44 (fumarate) | — |
| 5 | H₂N—⌬ | 52 (fumarate) | — |

EXAMPLE 6-9

Preparation of anilinofumarate

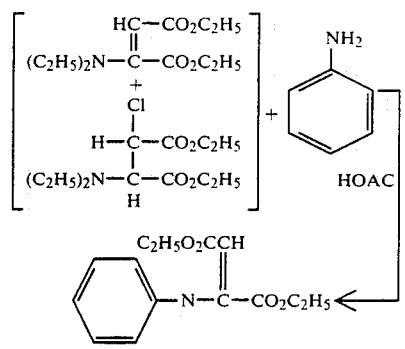

Aniline (0.93 g, 0.01 mol) is added to a toluene (20 mL) solution of acetic acid (3.0 g, 0.05 mol) and the mixture of diethyl diethylaminomaleate and diethyl 2-chloro-3-diethyl diethylaminomaleate and Example 2 above. The resulting solution was heated at 80° C. to 85° C. for 4 hours. After cooling the reaction mixture to room temperature, it is washed with water (10 mL) and then with aqueous HCl (12% w/w, 2 mL).

Analysis of the resulting toluene solution by gas liquid chromatography and isolation of the product indicate an overall yield of the sequence starting from diethylmaleate to be 69%.

Utilizing the above procedure the alkylaminomaleate and chloroalkylaminosuccinate mixtures obtained in Examples 2-5 give the yields of anilinofumarate based on starting diethylmaleate listed in Table II.

TABLE 2

| Example | Starting material of example | | % Yield for sequence starting from diethylmaleate or diethylfumarate |
|---|---|---|---|
| 7 | 3 | | 67% |
| 8 | 4 | | 38% |
| 9 | 5 | | 45% |
| 10 | 2 | no organic acid reflux for 10 hours | 40% |

EXAMPLE 10

Preparation of diethyloxalacetate and subsequent preparation of diethylanilinofumarate

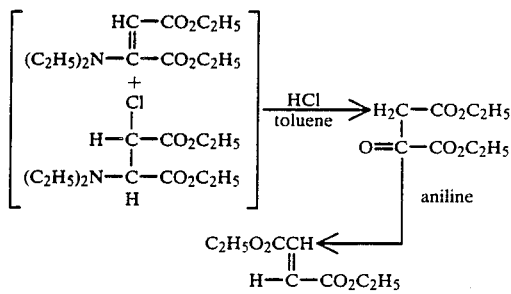

A toluene (15 mL) solution of a mixture of diethyl diethylaminomaleate and diethyl 2-chloro-3-diethylaminosuccinate (2.43 g, 0.01 mol) is prepared by the procedure of Example 2 above and is stirred with water (5.0 g) containing 2.15 g (0.015 mol) of concentrated HCl for two (2) hours and 30 minutes. The toluene layer containing diethyl oxalacetate is separated off and aniline (0.93 g, 0.01 mol) added. The resulting solution is stirred at room temperature for 30 minutes and then at reflux for one hour and 30 minutes while collecting the water which is formed in a Dean Stark collector. Analysis of the cooled toluene solution by gas liquid chromatography shows the yield of diethylanilinofumarate to be 55%.

EXAMPLE 11

Preparation of quinoline-2,3-dicarboxylic acid

Vilsmeier reagent is prepared by adding 4.61 g (0.03 mol) of POCl$_3$, dropwise, to a solution of 2.19 g (0.03 mol) of dimethylformamide in 12 mL of toluene, while maintaining the temperature at 20° C. to 30° C. The two layers are stirred at 20° C. to 30° C. for 60 minutes and then treated, dropwise, with a solution of 5.26 g (0.02 mol) of diethyl anilinofumarate prepared by the procedure of example 2 above, in 40 mL of toluene, while maintaining the temperature at 20° C. to 30° C. The solution that forms on heating is refluxed for 2 hours, cooled until reflux stops and is poured into 60 mL of water. The dark syrupy material that precipitates dissolves, when stirred at room temperature for 30 minutes. Analysis of the toluene solution by glc indicates a yield of 72%. Evaporation of the diester solution gives an oily low melting solid, which upon recrystallization from isopropyl alcohol gives 4.05 g of tan solid, mp 53°-56° C.

Two phases that are formed from 4.1 g (0.015 mol) of diester in 25 mL of toluene and 16 mL of 15% NaOH are refluxed with good mixing for 8 hours. The two phases are cooled to 50° C. to 55° C. and diluted with 20 mL of water. The aqueous phase is separated and added dropwise to 11 mL of 35% H$_2$SO$_4$, while keeping the temperature less than 40° C., and the resulting thick mixture is filtered, and the solid collected and dried overnight at 60° C./30–50 mmHg to yield 3.19 g of quinoline-2,3-dicarboxylic acid.

What is claimed is:

1. A method for the preparation of anilinofumarate, said method comprising: reacting a dichlorosuccinate of formula I $$Cl-CH-CO_2R$$
$$|$$
$$Cl-CH-CO_2R$$

I wherein R is C$_1$–C$_4$ alkyl, with a minimum of 3 molar equivalents of an amine of formula II $$R_1R_2NH$$

II wherein R$_1$ and R$_2$ are each H or C$_1$–C$_6$ alkyl, with the proviso that only one of R$_1$ or R$_2$ is H; or when taken together R$_1$ and R$_2$ with the nitrogen atom to which they are attached form a 5 or 6 membered ring containing at most 2 heteroatoms; in an inert solvent at a temperature of about 25° C. to reflux for about 1 to 24 hours; and further reacting the resulting mixture of formula IIIa alkylaminomaleate or alkylaminofumarate and formula IIIb chloroaminosuccinate

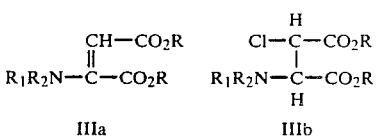

wherein R, R$_1$ and R$_2$ are as described hereinabove for formula I and formula II with a molar equivalent of aniline in an inert organic solvent containing an organic acid at a temperature of about 25° C. to 90° C. for about 1 to 24 hours.

2. A method according to claim 1, wherein said organic acid is acetic acid.

3. A method according to claim 2, wherein R is C$_2$H$_5$.

4. A method according to claim 3, wherein said formula II amine is diethylamine or morpholine.

5. A method according to claim 4, wherein said solvent is chlorinated hydrocarbon, chlorinated aromatic hydrocarbon, aromatic hydrocarbon, or mixtures thereof.

6. A method according to claim 5, wherein said solvent is ethylenedichloride, monochlobenzene, toluene or mixtures thereof.

7. A method according to claim 6, wherein said reactions are conducted at a temperature of about 75° C. to 85° C. for 2 to 9 hours.

* * * * *

UNITED STATES PATENT AND TRADEMARK OFFICE
CERTIFICATE OF CORRECTION

PATENT NO. : 5,001,254
DATED : March 19, 1991
INVENTOR(S) : Donald R. Maulding

It is certified that error appears in the above-identified patent and that said Letters Patent are hereby corrected as shown below:

Title Page, Item (73) Assignee: should read --American Cyanamid Company, Stamford, Connecticut Signed and Sealed this First Day of May, 2001

*Attest:*

NICHOLAS P. GODICI

*Attesting Officer*   Acting Director of the United States Patent and Trademark Office